(12) United States Patent
Ganesan et al.

(10) Patent No.: US 10,016,130 B2
(45) Date of Patent: Jul. 10, 2018

(54) EYE TRACKER SYSTEM AND METHODS FOR DETECTING EYE PARAMETERS

(71) Applicant: University of Massachusetts, Boston, MA (US)

(72) Inventors: Deepak Ganesan, Amherst, MA (US); Benjamin M. Marlin, Amherst, MA (US); Addison Mayberry, Fallon, NV (US); Christopher Salthouse, Newton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/257,868

(22) Filed: Sep. 6, 2016

(65) Prior Publication Data

US 2017/0188823 A1   Jul. 6, 2017

Related U.S. Application Data

(60) Provisional application No. 62/214,512, filed on Sep. 4, 2015.

(51) Int. Cl.
*G06K 9/00* (2006.01)
*A61B 3/113* (2006.01)
(Continued)

(52) U.S. Cl.
CPC .............. *A61B 3/113* (2013.01); *A61B 3/032* (2013.01); *G02B 27/0093* (2013.01); *G02B 27/017* (2013.01); *A61B 3/10* (2013.01); *G02B 2027/0178* (2013.01); *G02B 2027/0187* (2013.01)

(58) Field of Classification Search
USPC .................................................. 382/115–118
See application file for complete search history.

(56) References Cited

U.S. PATENT DOCUMENTS

| 4,145,122 A | 3/1979 | Rinard et al. |
| 5,231,674 A | 7/1993 | Cleveland et al. |
| (Continued) |

FOREIGN PATENT DOCUMENTS

| DE | 3541726 | 5/1987 |
| DE | 19731303 | 2/1999 |
| (Continued) |

OTHER PUBLICATIONS

Hansen et al., In the Eye of the Beholder: A Survey of Models for Eyes and Gaze. IEEE Transactions on, (32)3: 478-500. 2010.
(Continued)

*Primary Examiner* — Alex Liew
(74) *Attorney, Agent, or Firm* — Valauskas Corder LLC

(57) ABSTRACT

An improved eye tracker system and methods for detecting eye parameters including eye movement using a pupil center, pupil diameter (i.e., dilation), blink duration, and blink frequency, which may be used to determine a variety of physiological and psychological conditions. The eye tracker system and methods operates at a ten-fold reduction in power usage as compared to current system and methods. Furthermore, eye tracker system and methods allows for a more optimal use in variable light situations such as in the outdoors and does not require active calibration by the user.

17 Claims, 11 Drawing Sheets

(51) Int. Cl.
*A61B 3/032* (2006.01)
*G02B 27/00* (2006.01)
*G02B 27/01* (2006.01)
*A61B 3/10* (2006.01)

(56) References Cited

U.S. PATENT DOCUMENTS

| | | |
|---|---|---|
| 5,270,748 A | 12/1993 | Katz |
| 5,345,281 A | 9/1994 | Taboada et al. |
| 5,410,376 A | 4/1995 | Tasaka et al. |
| 5,481,622 A | 1/1996 | Gerhardt et al. |
| 5,632,742 A | 5/1997 | Frey et al. |
| 5,818,954 A | 10/1998 | Tomono et al. |
| 5,912,721 A | 6/1999 | Yamaguchi et al. |
| 5,926,251 A | 7/1999 | Okumura |
| 6,220,706 B1 | 4/2001 | Foley |
| 6,246,779 B1 | 6/2001 | Fukui et al. |
| 6,315,773 B1 | 11/2001 | Frey et al. |
| 6,578,962 B1 | 6/2003 | Arnon et al. |
| 6,637,883 B1 | 10/2003 | Tengshe et al. |
| 6,659,611 B2 | 12/2003 | Amir et al. |
| 7,280,678 B2 | 10/2007 | Haven et al. |
| 7,306,337 B2 | 12/2007 | Ji et al. |
| 7,331,671 B2 | 2/2008 | Hammoud |
| 7,391,887 B2 | 6/2008 | Durnell |
| 7,538,744 B1 | 5/2009 | Liu et al. |
| 7,620,216 B2 | 11/2009 | Hammoud |
| 7,653,213 B2 | 1/2010 | Longhurst et al. |
| 7,682,026 B2 | 3/2010 | Huffman et al. |
| 7,703,921 B2 | 4/2010 | Dick et al. |
| 7,783,077 B2 | 8/2010 | Miklos et al. |
| 7,809,160 B2 | 10/2010 | Vertegaal et al. |
| 7,832,866 B2 | 11/2010 | Chao |
| 8,032,842 B2 | 10/2011 | Kwon et al. |
| 8,135,173 B2 | 3/2012 | Chao |
| 8,177,363 B2 | 5/2012 | Sebastian et al. |
| 8,259,169 B2 | 9/2012 | Sugio et al. |
| 8,274,578 B2 | 9/2012 | Hong et al. |
| 8,494,229 B2 | 7/2013 | Jarvenpaa et al. |
| 8,860,660 B2 | 10/2014 | Jahnke |
| 8,885,882 B1 | 11/2014 | Yin et al. |
| 8,929,589 B2 | 1/2015 | Publicover et al. |
| 9,033,502 B2 | 5/2015 | Nistico et al. |
| 9,070,017 B2 | 6/2015 | Hennessey et al. |
| 2003/0118217 A1 | 6/2003 | Kondo et al. |
| 2003/0223037 A1* | 12/2003 | Chernyak ............ A61B 3/1015 351/209 |
| 2004/0181168 A1 | 9/2004 | Plant et al. |
| 2004/0189939 A1 | 9/2004 | Dick et al. |
| 2005/0207676 A1* | 9/2005 | Lin ....................... G06T 3/4023 382/299 |
| 2007/0140531 A1* | 6/2007 | Hamza ............... G06K 9/00597 382/117 |
| 2008/0137909 A1 | 6/2008 | Lee et al. |
| 2009/0109400 A1 | 4/2009 | Yoshinaga et al. |
| 2009/0196460 A1 | 8/2009 | Jakobs et al. |
| 2010/0092049 A1 | 4/2010 | Schroeder et al. |
| 2011/0182472 A1 | 7/2011 | Hansen |
| 2012/0230547 A1 | 9/2012 | Durnell et al. |
| 2013/0188834 A1 | 7/2013 | Ebisawa |
| 2014/0111630 A1 | 4/2014 | Pires et al. |
| 2015/0154758 A1 | 6/2015 | Nakazawa et al. |
| 2015/0160726 A1 | 6/2015 | Sullivan |

FOREIGN PATENT DOCUMENTS

| | | |
|---|---|---|
| WO | 2002031581 | 4/2002 |
| WO | 2004045399 | 6/2004 |
| WO | 2007076479 | 7/2007 |
| WO | 2012171405 | 12/2012 |

OTHER PUBLICATIONS

Pomerleau et al., Non-Intrusive Gaze Tracking Using Artificial Neural Networks. Technical Report, Pittsburgh, PA 1994.

Tan et al., Appearance-based Eye Gaze Estimation. WACV '02 Proceedings of the Sixth IEEE Workshop on Applications of Computer Vision. p. 191-195. 2002.

Ye et al., Detecting eye contact using wearable eye-tracking glasses. Proceedings of the 2012 ACM Conference on Ubiquitous Computing. pp. 699-704. 2012.

Mayberry et al., iShadow: Design of a Wearable, Real-Time Mobile Gaze Tracker. MobiSys. Jun. 2014;2014:82-94.

* cited by examiner

| Component | Power (4 Hz) | Power (278 Hz) |
|---|---|---|
| Camera | 7.30 μW | 30.8 μW |
| MCU (digitization) | 2.67 mW | 11.3 mW |
| MCU (computation) | 4.79 mW | 20.2 mW |
| NIR | 8.24 μW | 34.8 μW |
| Overall | 7.48 mW | 31.6 mW |

FIGURE 12

| Model | Pupil Size Error (pixels) |
|---|---|
| Neural Network | 0.50 |
| Cross | 0.85 |

FIGURE 13

| Feature | Mean Difference (pixels) |
|---|---|
| Pupil Center | 0.853 |
| Pupil Size | 1.52 |

EYE TRACKER SYSTEM AND METHODS FOR DETECTING EYE PARAMETERS

CROSS-REFERENCE TO RELATED APPLICATIONS

This application claims priority to U.S. Provisional Patent Application 62/214,512 filed Sep. 4, 2016, incorporated herein by reference.

FEDERALLY SPONSORED RESEARCH OR DEVELOPMENT

This invention was made with government support under 1217606, 1218586, and 1239341 awarded by The National Science Foundation and 1U54EB020404 awarded by The National Institutes of Health. The government has certain rights in the invention.

FIELD OF THE INVENTION

The invention relates generally to video oculography, i.e., gaze tracking using eye images. More specifically, the invention relates to a highly optimized low-power wearable eye tracker and methods for detecting eye parameters including eye movement, pupil center, pupil diameter (i.e., dilation), blink duration, and blink frequency. These parameters may then be used to determine a variety of physiological and psychological conditions.

BACKGROUND OF THE INVENTION

The human eye offers a fascinating window into an individual's personality traits, medical problems, brain abnormalities, behavioral conditions, cognitive attention, and decision making. These characteristics have made it the subject of decades of research by experts in cognition, ophthalmology, neuroscience, epidemiology, behavior, and psychiatry, who have not only enhanced the understanding of how the eye works, but also revealed new ways of diagnosing health concerns. For example, nearly every health condition that affects the brain causes substantial variations in eye movement patterns including attention deficit hyperactivity disorder (ADHD), Autism, Williams syndrome, Schizophrenia, Parkinson's, Alzheimer's disease, Depression, and others.

Despite the enormous potential for advancing detection of health states and understanding of human decision making by measuring the eye, progress has been stymied by the lack of wearable eye trackers that are integrated into a regular pair of eyeglasses. The design of a low-power wearable eye tracker is remarkably challenging from the computation, sensing, communication, and aesthetic design perspectives. A real-time eye tracker involves an eye facing imager sampling at frame rates of tens of Hz (up to 100 Hz to detect fine-grained eye movements or saccades) thereby generating megabits of data per second and making communication to a phone extremely power-hungry. As a reference point, the Google Glass optical head-mounted display lasts only a few hours when streaming from its outward facing camera, while running too hot for comfort. Real-time computation on the eyeglass is also remarkably challenging, particularly given the volume of data and complexity of the image processing techniques. While the focus in is on the computation and power aspects, aesthetic design presents an equally significant challenge since the sensors need to be embedded in an unobtrusive manner within an eyeglass frame.

While many eye trackers are available for commercial use, they are expensive, power hungry and relatively bulky, which makes them less than ideal for regular use. Several efforts have been made to design low-power wearable eye trackers, but many challenges remain. For example, power consumption is a major avenue for improvement in eye trackers with some consuming 1.5 W and more optimized eye trackers consuming around 70 mW. These numbers are still much higher than typical wearables which only consume a few milliwatts of power, so there is a need to enable long-term operation of eye trackers on small wearable batteries.

Another desired improvement is robustness. Eye trackers simply do not work outdoors given the variability in outdoor lighting conditions. More generally, achieving robust operation in environments with different illumination conditions is extraordinarily challenging and has not been achieved so far by either research prototypes or bulkier commercial products. While some eye trackers rely on visible light, they fail under poorly illuminated conditions. Many commercial eye trackers use near-infrared (NIR) illumination of the eye, but fail to operate effectively outdoors due to overwhelming ambient infrared light.

Continuous real-time tracking of the state of the eye (e.g. gaze direction, eye movements) in conjunction with the field of view of a user is profoundly important to understanding how humans perceive and interact with the physical world. Real-time tracking of the eye is valuable in a variety of scenarios where rapid actuation or intervention is essential, including enabling new "hands-free" ways of interacting with computers or displays (e.g. gaming), detection of unsafe behaviors such as lack of attention on the road while driving, and leveraging visual context as a signal of user intent for context-aware advertising. Continuous eye tracking is also useful in non-real-time applications including market research to determine how customers interact with product and advertising placement in stores, and personal health, where the state of the eye provides a continuous window into Parkinson's disease progression, psychiatric disorders, head injuries and concussions, and others.

While wearable devices provide insight into a variety of physiological and health conditions, one aspect that has lagged behind is the ability to infer an individual's cognitive state in real-time. There is significant need for a device that can continuously monitor fatigue, since this has implications for a wide range of safety-critical application domains. For example, in 2014 there were 846 drowsy-driving-related fatalities (2.6% of all fatalities) recorded in the National Highway Traffic Safety Administration's (NHTSA) Fatality Analysis Reporting System (FARS) database. Being alert and conscious is not only crucial for drivers, but also for many other sensitive and important tasks. For example, if air traffic control (ATC) operators become distracted or their performance impaired, thousands of people could be put in danger. Similarly, other safety critical jobs include heavy machinery operators, power plant operators, and so on. Relying on self-awareness is not sufficient according to experts, both drivers and employees in sensitive positions fail to recognize their fatigue and drowsiness state. Therefore, there is a tremendous need for real-time, precise detection of the fatigued state in order to eliminate hazardous situations. Eye monitoring is a promising technology to address the aforementioned problems.

Eye movements are impacted directly by the underlying neural mechanisms of the brain, and therefore can provide useful information about the cognitive state of individuals. In order to continuously monitor the eye, remotely mounted cameras (e.g. on the dashboard of a car) may be used or eye measurement sensors embedded in a pair of spectacles. While the more common technology today is remotely mounted dashboard cameras for monitoring fatigue and drowsiness, these units rely on a user being in front of the camera.

Eye monitoring can be a much more viable technology for monitoring fatigue and drowsiness if the eye monitoring capability can be embedded in a regular pair of spectacles. Thus head-mounted eye monitoring is a much more viable technology for monitoring fatigue and drowsiness. Advantageously, wearable devices can continuously monitor eye movement in mobile settings useful for a broad range of applications such as detecting fatigue among medical professionals, detecting fatigue among shift workers, and others.

In addition, continuous measurements can also provide more information throughout the day, thereby providing advance warning about fatigue state prior to performing a safety critical activity such as driving. Furthermore, monitoring the eye in close proximity makes such a method more robust to the issues that are faced by remote eye monitors such as occlusions, head movements, variability in ambient lighting, and reflections due to spectacles or sunglasses. Thus, head mounted monitors can potentially provide higher accuracy detection than remote monitors.

Accordingly, there is a need for an eye tracking system that reduces power consumption and displays a more robust usefulness, such as for use in outdoors conditions. The present disclosure addresses these needs.

SUMMARY OF THE INVENTION

The invention is directed to a highly optimized low-power wearable eye tracking device—"eye tracker"—that tradeoffs between power and robustness to illumination conditions. According to the invention, an eye tracking device such as eyeglasses includes an imaging component, an illuminator component, a photodiode component and a controller, or special-purpose processor, such as a field-programmable gate array (FPGA)-style processing device. The controller may be integrated with the eye tracking device or reside remotely such as within another device such as a mobile device including, for example, a tablet or smart phone.

The controller processes image data according to stages—a search stage, refine stage. Additionally, the controller may perform a switching stage that ensures the controller is operating in a mode appropriate for the current environment, for example when a user is transitioning between an indoor and outdoor environment. More specifically, the invention operates in an indoor-outdoor-aware mode to deal with different illumination conditions and noise.

Advantageously, the invention sacrifices energy-efficiency and switches between the sensing and computational blocks activated depending on how much noise and variability is observed. This includes a staged processing pipeline with the search stage sampling more pixels of the image to get a better estimate of the pupil location, the refine stage refining the estimate by performing more computation on the pixels to deal with noise and using more complex models to estimate eye parameters. The first stage of the pipeline consumes 20 mW, which is more than an order of magnitude higher than the typical power consumption, but this is triggered less than 10% of the time, therefore overall efficiency does not decrease significantly.

The search stage operates with no prior knowledge of pupil location, and uses a neural network to obtain an estimate of pupil center and size from a subsampling of pixels. The search stage is an artificial neural network that uses a subsampling of image pixels to estimate the position of the pupil in the eye. The invention identifies the pupil within an image of an eye to record and output the center x, y coordinates as well as the radius of the pupil, giving an accurate position of the pupil in the eye.

There is no real-time decision about which pixels to sample, or how to map from pixel values to pupil output—it is simply computing a weighted combination of the sub-sampled pixels based on hard-coded parameters from the learnt neural network model. The online operation is therefore lightweight and easy to optimize in hardware.

The refine stage takes an estimate from the search stage, and uses a very fast and accurate procedure to locate and track the eye such as the center of the pupil. When the refine stage loses track of the pupil due to specular reflections or other unpredictable variations, it reverts to the search stage to get another estimate of the eye location.

The two stages differ in terms of the amount of sensing required (i.e. number of pixels acquired per frame from the imager) as well as the amount of computation performed to extract eye parameters from the pixels.

In certain embodiments, the invention may switch from an indoor to outdoor mode of operation. In outdoor settings, illumination such as NIR illumination is turned off (since there is too much ambient infrared), switches to different camera parameters to deal with outdoor lighting, and switches the neural network model to one that is trained for outdoor conditions. Indoor versus outdoor conditions are detected using the photodiode component that tracks the level of ambient infrared light. In the outdoor stage, the processor does not use the refine stage and only relies on the neural network to track the eye.

Additionally, the use of an illuminator component provides an optimum environment for tracking the pupil by providing controlled lighting conditions. Use of NIR according to the invention is very different from methods used by commercial eye trackers. Typical eye trackers use multiple narrow NIR beams, and process the image data to locate these NIR beams, before combining this information with an eye model. However, this process requires several NIR LEDs, more complex geometric methods for estimating eye parameters, and does not generalize to outdoor settings. In contrast, the invention uses just two NIR LEDs, very simple models, and computational methods that continue to work in outdoor settings. Use of two modes, along with an illuminator component allows the invention to obtain a very accurate determination of pupil center and size not possible in the current art except at significantly higher levels of power consumption.

The invention provides a graceful tradeoff between robustness and power under typical indoor illumination, by spending most time in the fastest and most efficient stage while occasionally using the neural network to provide estimates. In outdoor illumination, all processing time is spent in the slower but more robust neural network stage.

Robustness issues are also addressed by a model training pipeline that operates with no input from the user. For example, whenever the eye tracking device is fully charged or has good connectivity, a block of images can be communicated to the processor or other computational device, and a new model trained offline. This enables the generation of accurate labels of pupil center and dilation from noisy image data (collected either indoors or outdoors), which makes it possible to learn the neural network models with zero effort from the user.

According to the invention, pupil center and pupil dilation can be estimated simultaneously, thereby providing two key measures of the eye in real-time. The estimate of pupil center may be used, for example, to determine the gaze direction of the user.

The invention also contemplates an eye tracker including special-purpose processor that extracts key features of fatigue at low power and high frame rate. More particularly, blink duration and blink frequency may be determined using upper eyelid and lower eyelid parameters for eye closure and blink-related features. As such, the entire image does not need to be sampled. Instead, a small slice of pixels (such as a few columns) can be captured and processed to extract the salient features for fatigue detection. Using a minimal set of pixels the proportion of the time that the eyes are 80% to 100% closed, excluding blinks, is measured. This may be done by using a template matching algorithm that operates on the time-series of the signal and can extract blinks of different types and durations. Once blinks are identified, blink features such as duration can be extracted and blinks can be removed from the data allowing further processing to extract blink duration and blink frequency.

The invention operates at very high frame rates (exceeding 100 fps) during typical operation using an optimized staged processing pipeline. This capability is particularly useful for detecting small fine-grained saccadic movements which happen while reading or when fatigued, providing further window into an individual's neural activities.

With optimization for the common case, more power-hungry features are left to deal with the more difficult but uncommon scenarios that occur such as antagonistic environments involving outdoor sunlight, shadows, and specular reflection. Specular reflection may include that resulting from an onboard illumination source from off the cornea.

The invention is optimized heavily for the common case that a) users spend a substantial fraction of time indoors (homes, shopping malls, etc.), and b) 80% of the time is spent by a user fixating on points, during which time the eye moves only a small amount (referred to as microsaccades, which are typically less than 0.40). The invention optimizes for this regime by using a small amount of near-infrared illumination, a few tens of pixels sampled per estimate, and a few dozen instructions executed per pixel to estimate eye gaze and pupil dilation parameters. Advantageously, the invention realizes a power consumption for the common case at about 7 mW in contrast to current known systems consuming up to three orders of magnitude difference (1.5 W) and even up to an order of magnitude (70 mW) difference.

According to the invention, pupil centers may be tracked with accuracy of roughly 1 pixel (0.3°) and pupil dilation with accuracy of approximately 1 pixel (0.22 mm) in indoor lighting conditions. In addition, the invention adjusts to indoor and outdoor illumination using an indoor-outdoor near-infrared (NIR) sensing component with pupil center error increasing only by a modest amount in outdoor settings (4 pixels or 1.2°). Another advantage of the eye tracker according to the invention is that it operates end-to-end at a total power budget of 7.5 mW when running at 4 Hz, which 10× less than that currently known in the art. Alternatively, invention can achieve eye tracking rates of upwards of 250 frames/second by scaling power consumption up to 32 mW.

In particular, the controller and an IR photodiode detect an outdoor lighting condition. In response, the controller adjusts various camera parameters, such as the gain function, to be better suited to capture images and pixels in the outdoor lighting condition. The controller also hard-codes a previously calibrated model optimized for outdoor lighting conditions. The controller further omits the tracking step and solely relies upon the estimating step to determine the location and size of the pupil. In this way, the controller increases the robustness of the eye tracking platform at a modest cost in power consumption.

Accordingly, some embodiments of the invention provide for a system and method for tracking eye movement comprising an imaging component comprising a camera positioned to image the pupil. A controller is configured to obtain a subsampling of a set of pixels gathered from the camera and estimate, based on the subsampled set of pixels, the center of the pupil by determining a center x and y coordinates of the pupil, as well as the radius r of the shape of the pupil. The system further tracks the center of the pupil, and the size of the pupil by sampling a row and a column of pixels based on the estimate of the center of the pupil location.

The tracking step can further include median filtering the row and column of pixels, detecting regions of the eye using edge detection, finding the midpoint of the row and column of pixels, performing a validity check to determine the midpoint is consistent, and if the validity check shows an error, the controller repeats the estimate step and tracking step.

The system and method can further comprise a calibration step wherein the controller captures images of the eye in at least one lighting condition and communicates the images to a computing device which performs the estimating step and the tracking step to form a signature of the eye in that particular lighting condition. After the calibration step, when the controller detects that particular lighting condition, the signature is hard-coded into the controller for use during the estimating step. The calibration step can be completed automatically, without any active participation by the user.

The invention may be utilized in a variety of applications, for example, as treating or diagnosing neurological disorders such as ADHD, Autism, Williams syndrome, Schizophrenia, Parkinson's, Alzheimer's disease, Depression, learning disorders, ocular diseases and fatigue.

These and other exemplary features and advantages of the present invention will become clear from the following description with reference to the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which:

FIG. 12 illustrates a table of the power breakdown of component according to the invention.

FIG. 13 illustrates a table of pupil radius estimation accuracy according to the invention.

DETAILED DESCRIPTION OF THE INVENTION

The invention detects eye parameters using a staged architecture that trades off power for robustness. The architecture uses an optimized detector for the "common case" involving a user being indoors and in limited-noise settings, and tremendously reduces the overall power consumption down to numbers that are within the range of typical wearable devices. Noise and variable illumination settings are dealt with by using more computational and sensing heft to filter out noise and deal with variability. Very high frame rates are achieved providing the ability to sense fine-grained eye parameters. Most surprisingly, all of this functionally is achieved while operating on a small controller such as an ARM Cortex M3.

Figure 1:
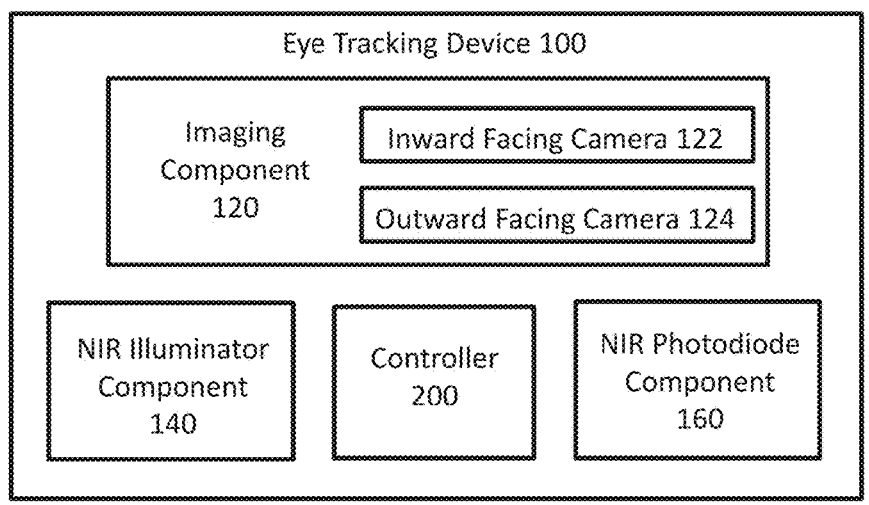
FIG. 1 is a block diagram of an eye tracking system for detecting eye parameters according to the invention.

The eye tracking system for detecting eye parameters illustrated in FIG. 1 is directed to a device 100 such as an eyeglasses. An imaging component 120, such as a camera, is mounted on the device 100. In certain embodiments the imaging component 120 includes an inward facing camera 122 mounted on a lower part of the eyeglass frame facing the user's eye. The placement of the inward facing camera 122 is low on the eyeglass frame since it is a natural tendency for users to look downward often. With a camera mounted in the lower position it is observed that, when looking down, a user's pupil is pointed nearly directly at the camera, making detection easier. In addition, when the user looks down for any reason, the upper eyelid naturally lowers a little. This can obscure the eye features when viewed from a higher vantage point—the lower eyelid does not noticeably raise when looking up, so the eye does not become obscured even when viewed from a lower angle. In addition, the imaging component 120 may include a second outward facing low power camera 124.

According to a particular embodiment, the imagining component 120 in FIG. 1 is a Stonyman Vision Chip produced by Centeye, Inc. (Stonyman), which provides a resolution of 112×112 pixels, each of which is characterized by a logarithmic voltage response to lighting conditions. These pixels have a high dynamic range, and more importantly, allow a random-access interface provided by a register-based control scheme. Besides the extremely low power consumption compared to off-the-shelf cameras (3 mW), the main advantage of the Stonyman imaging component is that it allows for random access to individual pixel values permitting sub-selection of specific pixels significantly reducing digitization cost. Another important characteristic of the Stonyman imaging component is that camera gain parameters are controlled programmatically rather than automatically (i.e. there is no automatic gain control like in other cameras). The ability to control gain is beneficial to adjust gain parameters and the model parameters in tandem when triggered by the NIR photodiode 160. Finally, the Stonyman camera also provides features such as a sleep mode, during which the pixel acquisition circuitry can be powered down. The low-power state has power consumption less than half a microwatt since only a few control registers are running to maintain camera state.

As seen in FIG. 1, the eye tracking device 100 includes a near-infrared (NIR) illuminator component 140 and NIR photodiode component 160. The NIR illuminator component 140 and NIR photodiode component 160 are mounted, such as within an eyeglass frame, to detect ambient NIR levels. The NIR illuminator component 140 is to illuminate the pupil for more accurate imaging. The inward facing camera 122 may also have an infrared (IR) filter to capture an illuminated eye. The NIR Illuminator component 140, such as a pair of NIR LEDs is located on the device 100 to provide best illumination while minimizing issues due to specular reflections. The NIR photodiode 160 detects the level of ambient NIR and allowing detection of indoor conditions versus outdoor conditions.

It is also contemplated that the eye tracking device 100 may have other sensors and wireless communication capabilities such as Bluetooth to communicate with external devices such as controller 200 that resides within another device such as a mobile device. However, it is also contemplated that controller 200 may be integrated with the eye tracker 100 such as mounted on an eyeglass frame. The controller 200 may be an STM32L151 microcontroller, which is manufactured by STMicro Corporation and is an implementation of the Cortex M3 standard. It other embodiments the controller 200 may be a field-programmable gate array (FPGA)-style processing device. The controller 200 provides a rapid switching loop between the search stage and the refine stage. However, the optimization function is solved offline using labeled training data to increase speed and accuracy while reducing power of the controller. The parameters are then hard-coded into the tracking device.

Figure 2:
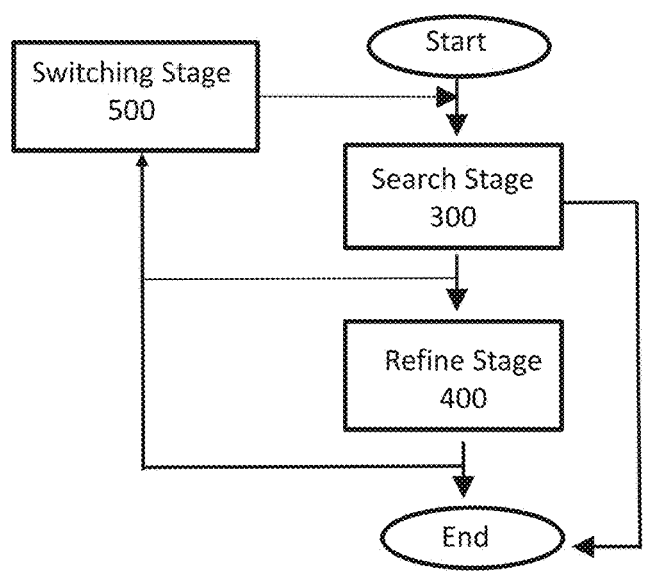
FIG. 2 is a flow chart of an optimized staged processing pipeline according to the invention.

FIG. 2 is a flow chart of an optimized staged processing pipeline according to the invention. A search stage 300 is an estimating step that uses a neural network to get an initial estimate of pupil location. A refine stage 400 is a tracking step that zones in on exact pupil center and performs rapid tracking unless the pupil is missed. The switching stage 500 is used to determine between indoor and outdoor modes of operation. The invention operates using two different modes to optimize robustness and power consumption. In indoor conditions, the invention operates in both the search stage 300 and refine stage 400. However, the outdoor mode requires only the search stage 300. The switching stage 500 ensures the controller is operating in a mode appropriate for the current environment, for example when a user is transitioning between an indoor and outdoor environment.

Figure 3:
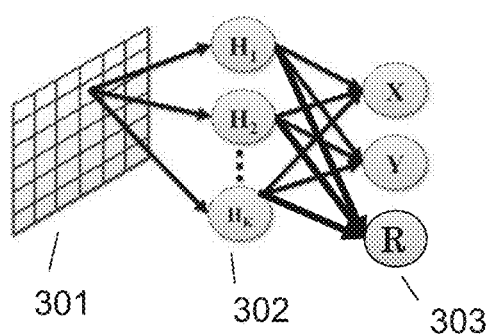
FIG. 3 illustrates the neural network gaze/pupil prediction model according to the invention.

The search stage 300 is an artificial neural network (ANN) prediction model as shown in FIG. 3 that operates over a subsampled set of pixels. As shown in FIG. 3, the input 301 is an array of pixel values of an image obtained from the imaging component, and the output 303 is a predicted (x,y,r) pupil coordinates and size. Between the input 301 and output 303 exists a hidden layer 302 of hidden units. In addition to determining the parameters of the neural network, a smaller subset of pixels is also determined to sample to reduce power consumption, while achieving comparable pupil prediction accuracy.

The problem is set up as a bi-objective optimization, where one objective is to minimize the set of pixels that need to be sampled to reduce power consumption, and the second objective is to minimize loss in pupil center prediction accuracy. This is achieved using a neural network learning algorithm together with a regularizer that penalizes models that select more pixels. The optimization problem has two terms: a) an error term that captures how well the algorithm predicts pupil coordinates and size, and b) a penalty term that increases with the number of pixels selected. To promote sparsity (i.e., to select a small active pixel set to sample), the algorithm uses a sparsity-inducing $l_1$ regularization function, which minimizes the number of pixels sampled. The optimization function is solved offline using labeled training data, and the parameters are hard-coded into the tracking device for real-time prediction of the pupil center.

Figure 4:
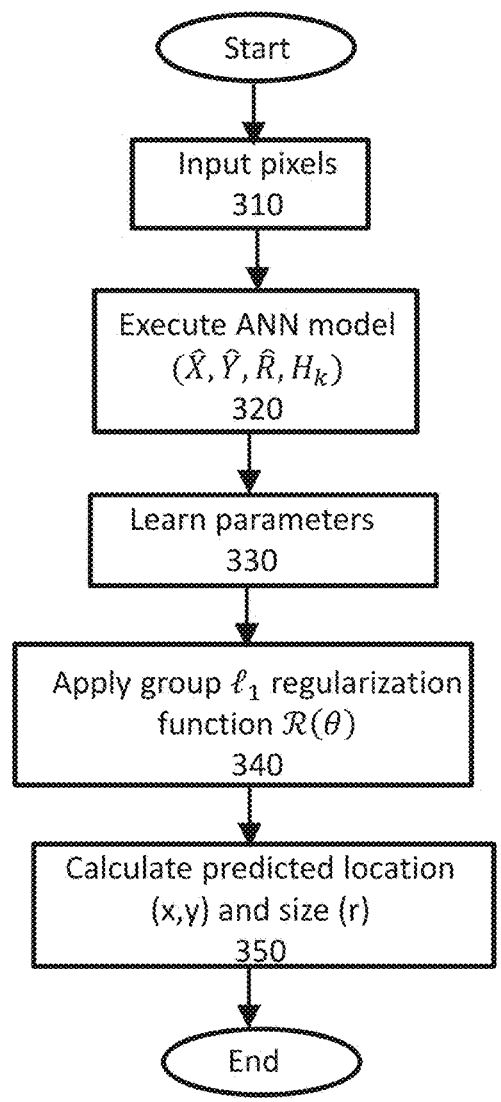
FIG. 4 is a flow chart of the estimating steps performed by the search stage according to the invention.

FIG. 4 is a flow chart of the steps performed by the search stage according to the invention. The input at step 310 to the neural network is still the subsampled pixels, however it is now trained to minimize error over three target values-center x, center y, and radius R. The input layer 301 is a D×D array of values I representing the eye-facing image. The pixel at row i and column j is given by $I_{ij}$. The desired output of the system has three components: the horizontal and vertical coordinates of the pupil center in the eye-facing image plane, (X,Y), and the radius of the pupil, R. The model is executed at step 320 which includes a hidden layer consisting of K hidden units $H_k$. The model includes input-to-hidden parameters $W_{ijk}^{IH}$ for each pixel location (i,j) in the eye-facing image and each hidden unit $H_k$; a hidden unit bias parameter B for each hidden unit $H_k$; hidden-to-output parameters $W_{kx}^{HO}$ and $W_{ky}^{HO}$ mapping between hidden unit $H_k$ and the outputs—pupil coordinates (X,Y) and radius R; and output bias parameters $B_x^O$, $B_y^O$, $B_r^O$ for these outputs. The hidden units use a standard hyperbolic tangent (tan h) activation function. The output units use linear activations. The artificial neural network (ANN) is given below:

$$\hat{X} = B_x^O + \sum_{k=1}^{K} W_{kx}^{WO} H_k$$

$$\hat{Y} = B_y^O + \sum_{k=1}^{K} W_{ky}^{HO} H_k$$

$$\hat{R} = B_r^O + \sum_{k=1}^{K} W_{kr}^{HO} H_k$$

$$H_k = \tanh\left(B_k^H + \sum_{i=1}^{D}\sum_{j=1}^{D} W_{ijk}^{IH} I_{ij}\right)$$

Given a data set $D=\{I^n, X^n, Y^n\}_{n=1:N}$ consisting of N eye images $I^n$ with corresponding pupil parameter values ($X^n$, $Y^n$, $R^n$), the complete set of neural network model parameters $\theta=\{W^{IH}, W^{HO}, B^H, B^O\}$ is learned at step 330. The parameters are learned by minimizing a regularized empirical loss function between the neural network's predicted outputs ($\hat{X}^n$, $\hat{Y}^n$, $\hat{R}^n$) and the true outputs ($X^n$, $Y^n$, $R^n$). Squared error is used as the loss function. The objective function $\mathcal{F}(\theta|D)$ is shown below for an arbitrary regularization function $\mathcal{R}(\theta)$ with regularization parameter $\lambda$.

$$\mathcal{F}(\theta|D) = \sum_{n=1}^{N} \left(\hat{X}^n - X^n\right)^2 + (Y^n - Y^n)^2 + \lambda \mathcal{R}(\theta)$$

The objective function $\mathcal{F}(\theta|D)$ cannot be analytically minimized with respect to the model parameters $\theta$, so numerical methods are required. The gradients of the model parameters with respect to the loss can be efficiently computed using the standard backpropagation algorithm. For standard, smooth regularization functions the two norm squared $\|\theta\|_2^2$, the gradients of the regularization function $\mathcal{R}(\theta)$ are also easy to obtain. The base model can be learned using any numerical optimizer, for example, the limited memory BFGS algorithm.

Given that the eye-facing images are extremely redundant, the eye facing images can be drastically sub-sampled while preserving much of the accuracy. Pixels actually selected are referred to as active pixels. The set of active pixel locations selected using a binary mask A where $A_{ij}=1$ if the pixel is active and $A_{ij}=0$ if the pixel is not active. Given such an active pixel mask A, the neural network can be modified to base its prediction on the active pixel locations only. This corresponds to simply removing all of the edges between the inactive pixels and the hidden units (FIG. 3). The computation and communication complexity of image acquisition and pupil estimation are both linear in the number of active pixels such that a linear decrease in the energy cost of both image acquisition and prediction occurs as the number of pixels decreases.

To select a smaller active pixel set, a state-of-the art sparsity-inducing group-$l_1$ regularization function is used as shown at step 340 in FIG. 4. The neural network has one parameter between each pixel in the image and each hidden unit. To solve the subset selection problem all of the outgoing connections from a group of pixels is simultaneously set to zero. Any group-$l_1$ regularization function may be used such as the $l_1/l_2$ regularization function as shown below with only the input-to-hidden layer weights regularized. The groups consist of all of the parameters from a given pixel to each of the K hidden units.

$$\mathcal{R}(\theta) = \sum_{i=1}^{D}\sum_{j=1}^{d}\left(\sum_{k=1}^{K}(W_{ijk}^{IH})^2\right)^{1/2}$$

The neural network model parameters can then be learned by optimizing $\mathcal{F}(\theta|D)$ with the choice of regularizer given above. At step 350 the predicted or estimated pupil coordinates and size (x,y,r) are calculated.

Figure 5:
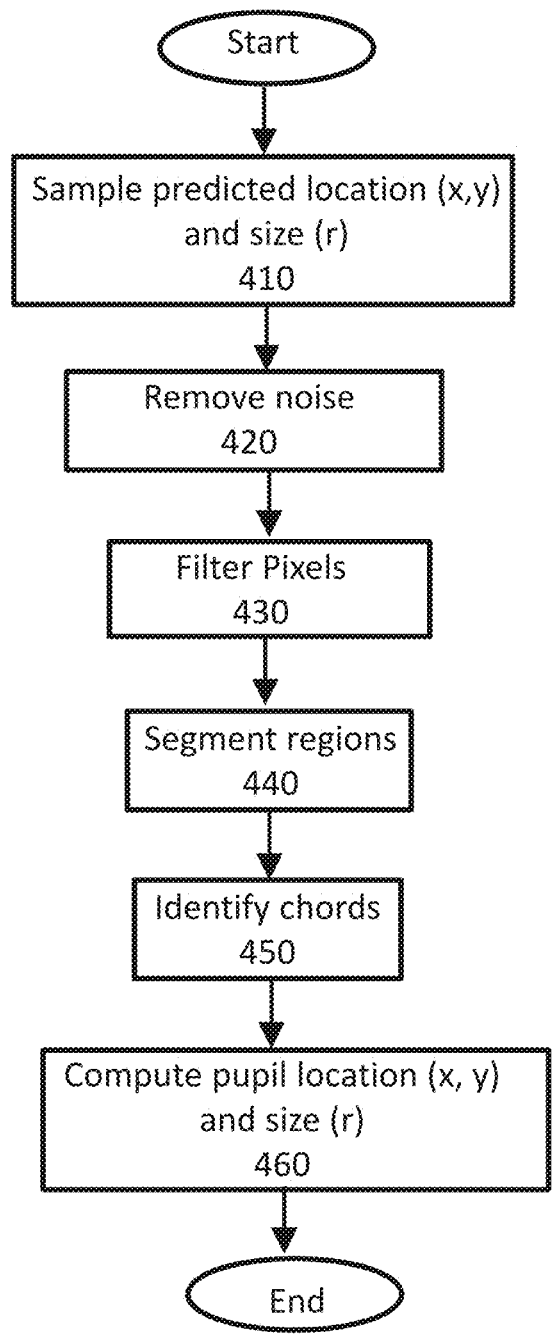
FIG. 5 is a flow chart of the tracking steps performed by the search stage according to the invention.

The estimated estimates are then subject to the refine stage 400 (FIG. 2). It should be noted that when operating in the outdoor mode, the refine stage 400 is eliminated. FIG. 5 is a flow chart of the tracking steps performed by the refine stage. The refine stage is a cross search model that uses a pupil location estimate from the search stage to track the center of the pupil. More specifically, the cross model leverages the estimate from the neural network to track the center of the pupil and pupil size with minimal sampling overhead.

At step 410, one row and one column of pixels at the estimated location of the pupil according to the search stage input is sampled. At step 420, any noise such as that from the user's imaging component, is removed, for example subtracting a fixed pattern noise mask per column and per row from the measured values to obtain the actual signal. Once the fixed pattern noise has been removed, the pixel values are median filtered at step 430. At step 440 regions of the eye are segmented into several regions—Sclera, Iris, Pupil—using edge detection that convolves the pixels with a box filter. Two chords are identified at step 450 corresponding to the pupil along the vertical and horizontal axes (i.e., the same steps are run on a column and a row of pixels). At step 460, a circle is fitted to the chords to compute pupil size and the mid-point of the circle computes the pupil location.

The refine stage can be performed extremely fast and requires few pixels, which in turn keeps power consumption as a minimum. Moreover, during this process, the controller can detect, through the infrared photodiode component, changes in lighting conditions and recalibrate, or load a previously stored calibration model to optimize pupil estimation.

The invention also provides for a switching stage 500 (FIG. 2) for operation between indoor-outdoor modes. In one embodiment, an IR diode incorporated into the frame of the glasses facing outward can detect the IR levels and determine whether the user is outside or inside. Once outside, the controller can adjust the imaging component parameters (such as camera gain) to account for the outdoor light. Furthermore, the controller can switch calibration models to one that is optimized for outdoor use. As mentioned previously above, the refine stage is not used in an outdoor setting. Instead, more complex calibration models are used that subsample more pixels to continuously operate in search stage, which increases power consumption but also allows for better outdoor performance.

Figure 6:
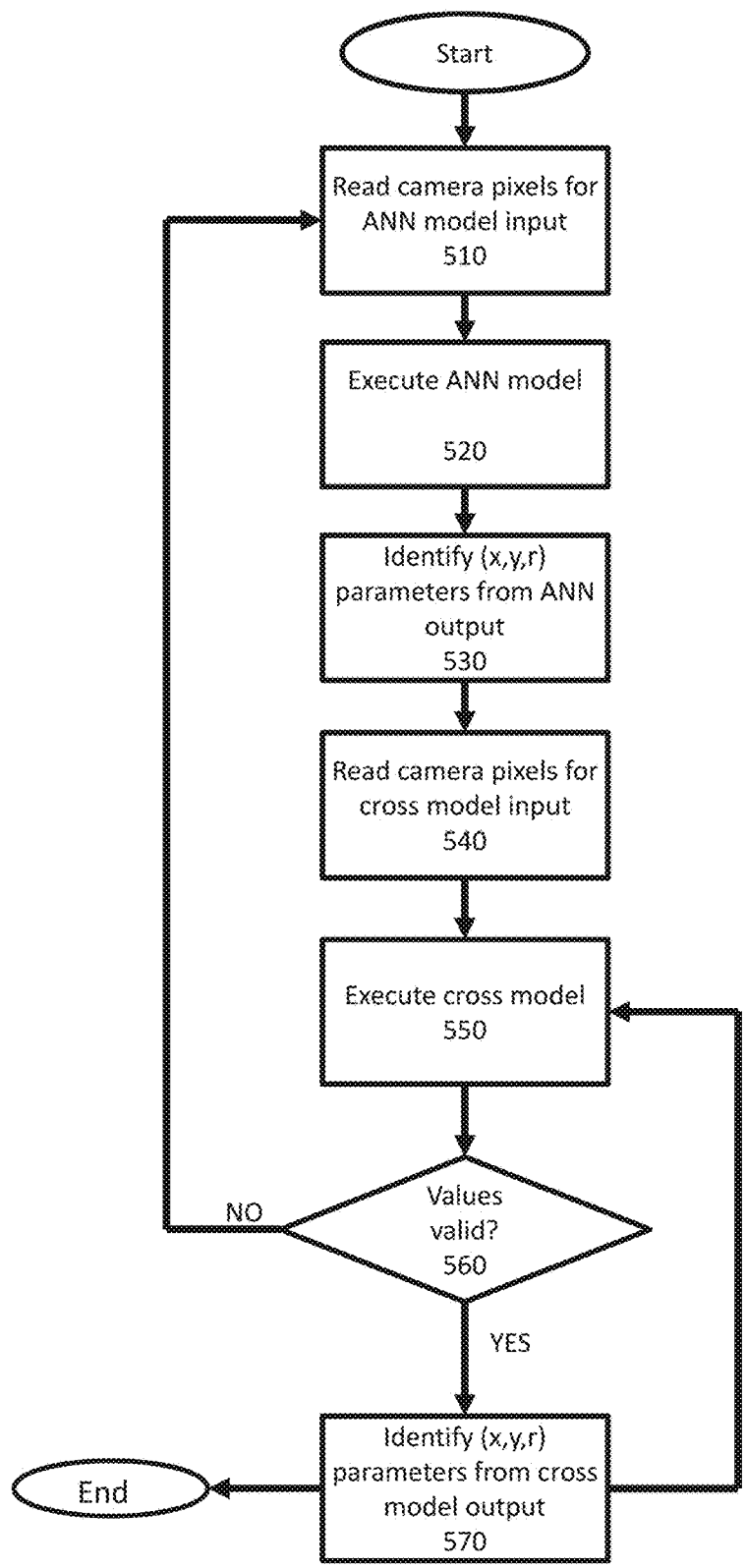
FIG. 6 is a flow chart of the steps performed by the switching stage according to the invention.

FIG. 6 is a flow chart of the steps performed by the switching stage according to the invention. The switching stage ensures the controller is operating in a mode appropriate for the current environment, for example when a user is transitioning between an indoor and outdoor environment. At step 510, the subsampled imager pixels are input to the ANN model of the search stage. After the ANN model of the search stage executes at step 520, the parameters (x,y,r) are identified at step 530. Control is then handed to the cross model found in the refine stage.

At step 540, the subsampled imager pixels are input to the cross model of the refine stage and the cross model executes at step 550. The cross model is extremely fast, and takes a fraction of the time of the ANN model, so it can execute quickly and check if further tracking of the eye can be handled entirely by using the cross model. An internal validity check is performed at step 560 to see if the results obtained are consistent. Specifically, the cross model checks if the circle diameter and two chords result in a consistent solution. If the controller determines that the center location of the eye is being accurately tracked, operation continues and parameters (x,y,r) are identified at step 570. If there is an error such as that the refine stage misses the pupil, or loses the center of the pupil, through for example, blinking, the controller, it falls back to the ANN model (step 510) of the search stage for another estimation of pupil center location and the estimate is again delivered to the refine stage. This process can be repeated as necessary. Since the cross model is fast, any misses are quickly handed by the ANN model within a short time window, so that the time window during which there is no estimate of the eye parameters is tiny.

The speed at which the cross model operates means that it is not only refining the estimate from the ANN model, but is also tracking the eye. The cross model can operate at frame rates of several hundreds of Hz, which is much faster than the speed at which larger saccades occur. As a result, even if the eyeball is moving, the cross model makes small adjustments each frame, thereby tracking the eye. The only occasions when the cross model fails is when there are blinks, specular reflections, shadows, or other artifacts, in which case it switches to the neural network.

One of the key enablers of the rapid switching controller described above is NIR-based illumination of the eye. Even though indoor lighting can vary significantly, there is virtually zero infrared content in the light emitted by lightbulbs (FL, CFL, LED, etc.) providing an opportunity to use a small NIR light source to illuminate the eye, and use an NIR-pass filter on the imaging component to make sure that only the NIR illuminated content is captured. This gives very controlled lighting conditions despite potential changes in the indoor lighting level.

With typical NIR LEDs having high power consumption the invention contemplates two ways to reduce NIR power consumption: (1) duty-cycle the NIR photodiode, and (2) reduce the operating voltage of the LED. NIR duty-cycling can be done between frames, therefore the reduction in number of pixels acquired using the cross-search model plays a significant role in the duty-cycling benefits. Reducing the operating voltage of the LED is effective as well with NIR LEDs operating down to about 1.15V, while reducing the voltage results in increased noise, leaving a sufficient signal for the neural network to learn a robust mapping. The combination of duty-cycling and low voltage operation reduces the NIR power budget by roughly two orders of magnitude, from 180 mW to less than a milliwatt.

The switching stage according to the invention occurs between indoor and outdoor modes of operation. Indoor and outdoor operation are very different for two reasons: (1) NIR illumination is useful in indoor settings since it provides a controlled environment for eye tracking, but not for outdoor settings where there is too much ambient IR, and (2) camera gain parameters need to be adjusted for outdoor settings and this requires modification of the neural network parameters.

According to the invention, a separate infrared photodiode that is built into the tracking device (facing outward rather than inward) is used. The IR levels are used to switch between different camera parameters (gain settings), as well as different neural networks trained for different conditions. The invention uses two models corresponding to specific ambient IR settings, and switches both the hardware parameters of the camera and the model based on the observed settings.

The switching process itself is extremely simple from the perspective of the firmware, requiring only a few MCU instructions to sample the photodiode at regular intervals. Since lighting conditions can be reasonably expected not to change with high frequency (i.e. more than once every few seconds), this sampling can be done as infrequently as once a second or less. If the MCU detects a significant change in lighting conditions, altering the camera gain parameters also only requires a small handful of instruction cycles. Thus, the overall power and time cost of the switching process is negligible.

Although in indoor settings, more power is consumed due to NIR illumination of the eye, but much more power is saved by reducing the number of pixels sampled and associated computation. In outdoor settings, the NIR LED is shut off and ambient IR is opportunistically leveraged to save power. The invention then relies on a more complex neural network model, which implies more pixels and more computation, but gains robustness in the process.

Figure 7:
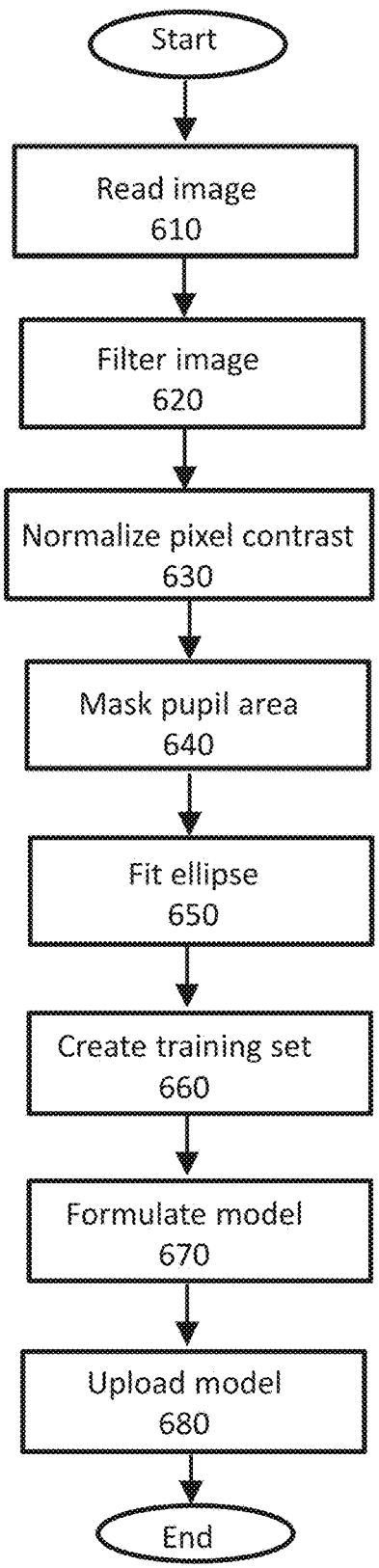
FIG. 7 is a flow chart of the steps performed to train the neural network model according to the invention.

FIG. 7 is a flow chart of the steps performed to train the neural network model according to the invention. These steps are performed offline. At step 610 an image is read. At step 620 the image is filtered using a median filter stage, from which the region corresponding to the eye is extracted. This region is further contrast-adjusted at step 630, and segmented to extract dark regions in the image. In good conditions, only the pupil shows up as a dark region. To address specular reflection of the NIR LED from the eye, (and when the specular reflection overlaps with the pupil, the dark region can look like a disk, or like a disk with a bite on the side), the pupil area is masked at step 640 using standard image-fill techniques. In particular, holes observed are filled in the segmented shape using standard image-fill techniques that identify distinctive regions of color within a larger area (the pupil) and adjust them using the surrounding pixels. Since the specular reflection is small relative to the size of the pupil, these simple techniques work extremely well. In outdoor conditions, shadows caused by the sun's position relative to the eyeglass frame may be seen and picked up by the segmentation block as shadowy regions. To isolate the pupil, the roundest segment to detect the pupil is desired. At step 650 an ellipse is fit to the pupil. The image data including coordinates and size of the pupil is used to create a training set at step 660. The training set is used to learn the neural network parameters and create a model that is uploaded at step 680 to the processor. These models may also be referred to as "calibration model" and can be created automatically without requiring active calibration by the user.

The search stage, or artificial neural network, can be calibrated. This calibration can be for different lighting situation and then the calibrated model (or signature) can be loaded into the processor for use in such conditions. For instance, the search stage can be automatically calibrated for outdoor use or low light use. When worn by the user and fully charged or in good connectivity, images can be captured and sent to a device for calibration. In this way, new calibration models can be archived and put in use when needed. By way of example, the user may go outside for a few minutes. Before returning inside, the imaging component has taken some images and sent them to a controller for the calibration step. The next time the user goes outside, the new calibration can be hard-coded into the controller and used to improve functioning of the device. In such a way, an archive of lighting conditions may be stored and put into use as needed.

Figure 8:
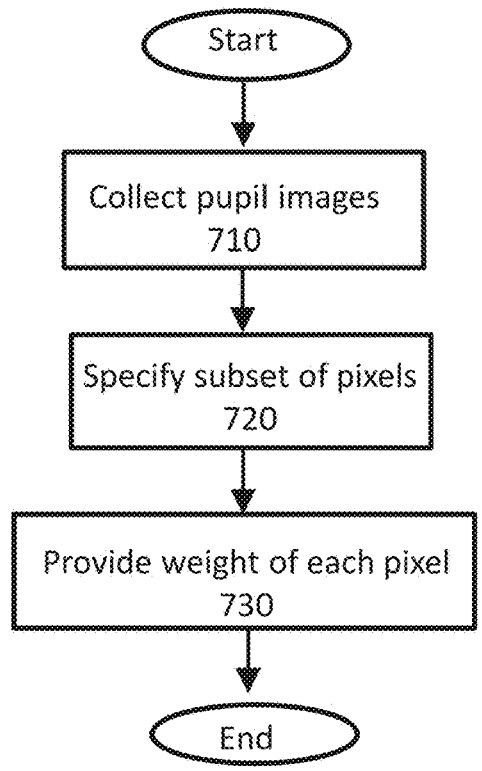
FIG. 8 is a flow chart of the steps performed to calibrate the neural network model according to the invention.

FIG. 8 is a flow chart of the steps performed to calibrate the neural network model according to the invention. At step 710, a series of images are collected of the pupil in various lighting conditions (e.g. outdoor, indoor, low light, bright light etc.) to determine the optimum parameters to locate the pupil. This process is performed offline. At step 720, the calibration step specifies which set of pixels to be subsampled. At step 730, the weight placed on each pixel is provided to estimate pupil location in the search stage. This calibration is provided to the controller on the eye tracking device, which uses the calibration in the search stage to estimate pupil location.

When the system encounters an outdoor lighting condition (or other instances of a large amount of infrared light), the system shifts into an outdoor mode. Here the search stage is recalibrated for outdoor lighting, or loads a previously calibrated search model for use in the outdoor lighting condition. The controller also adjusts camera parameters to optimized pupil imaging. The system then remains in the search stage and omits the refine stage. In this way, the system provides an accurate, fast and reliable determination of pupil location and size in a multitude of lighting conditions and using a lower amount of power as compared to current eye tracking systems.

Exemplary datasets were collected for evaluation. One dataset referred to as "indoor-stable" is directed to indoor-stable data (fixed pupil, fixed illumination) collected from 16 subjects, 12 male and 4 female. Each subject performed a video calibration routine where they looked at a high contrast dot moving on a computer monitor for several minutes. This gives good coverage of eye positions, and allows training of a good model as well as determines robustness to position of the eye. The illumination was held constant during this period, and subjects' pupils were roughly 5-7 pixels wide in this illumination. The subjects involved in the data collection represent a range of ethnic groups with different eye shapes and iris colorations. All subjects in the other datasets were also in the indoor-stable dataset.

Another dataset referred to as "indoor-variable" is directed to indoor-variable data (variable pupil, variable illumination) collected from 14 subjects, 10 male and 4 female. The lighting conditions were varied in five discrete levels using a combination of different sets of ceiling lights as well as target spotlights. The subject's pupils dilated between 5-pixels during this period, giving a fairly large range of pupil dilations that is representative of what one would observe in real-world settings. The screen brightness was kept low enough to not impact dilation much.

Another dataset referred to as "outdoor" is directed to outdoor data (uncontrolled illumination) collected from 3 subjects, all male, under outdoor settings. The conditions were generally bright and several minutes of data was obtained from each participant generally gazing at the outside scene under different orientations.

Yet another data set referred to as "indoor-outdoor" is directed to indoor-outdoor switching data collected for one subject, who walked between indoor and outdoor conditions repeatedly for four iterations, while spending roughly a minute in each environment. This dynamic setting helps evaluate whether the NIR photodiode-based model switching algorithm works effectively with real scene changes.

Ground truth labeling is performed on all datasets (indoor-stable, indoor-variable, outdoor, indoor-outdoor) for pupil center and pupil size using the methods as described above. Once labeled, the neural network was trained to identify the pupil center and radius of the best-fit circle approximating the pupil shape using a standard five-fold cross-validation scheme. The test set error was averaged over the five folds to get an average score. Pupil center error is computed as the L2 (Euclidean) distance between the estimate and the label, pupil size error as the difference between the estimated radius and the label. The errors were averaged over all subjects per model size to get a final set of error estimation accuracies over a range of neural network model sizes.

With the search and refine stages designed maximize estimation accuracy and power efficiency over a range of environmental parameters, results are evaluated for performance by comparing it against the two stages (search and refine) independently. Using the indoor-stable dataset in this evaluation provides an understanding of best case performance under limited dynamics. The following schemes were compared in this evaluation: artificial neural network (ANN) model, ideal cross model, and cross model.

The neural network model is learnt by varying λ (regularization parameter) to learn various models that have different tradeoffs between accuracy and pixels (which translates to power). This provides a pareto optimal set of solutions i.e. a set of solutions that shows the tradeoff between the two objectives.

The idealized cross method is initialized by the pupil center estimated offline. The cross model then estimates the pupil center and pupil size, and it is compared the accuracy against ground truth.

Figure 9A:
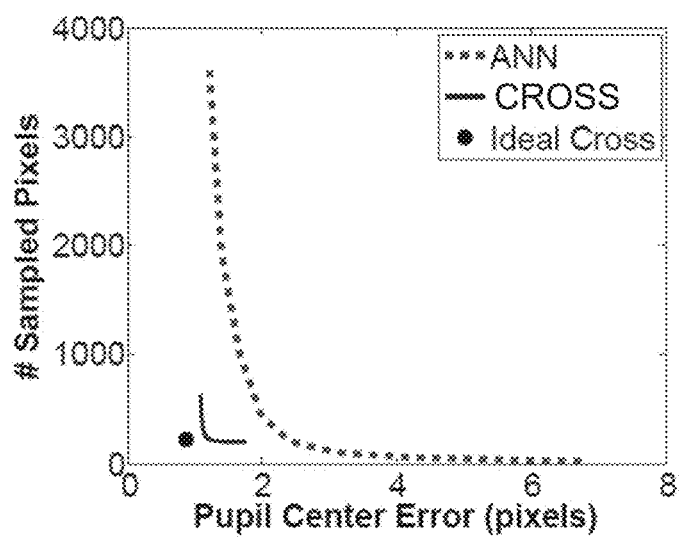
FIG. 9A illustrates a plot of sensing pixels versus center accuracy according to the invention.

Sensing, computation and NIR cost are evaluated. FIG. 9A shows the curve of sensing cost (in number of pixels sampled) against pupil center estimation error (in number of pixels). The curve is obtained by tuning the neural network regularization parameter, which allows for the generation of a number of network sizes with varying power needs and corresponding accuracy. The result clearly shows that there is a significant gap between any pareto optimal solution that can be obtained for the neural network versus the solution provided by the idealized cross model. The invention (denoted by "CROSS") operates between the two but closer to the idealized cross model. This can be explained by the fact that the neural network is triggered only about 10-15% of the time whereas the cross model operates the remaining 85-90% of the time.

Figure 9B:
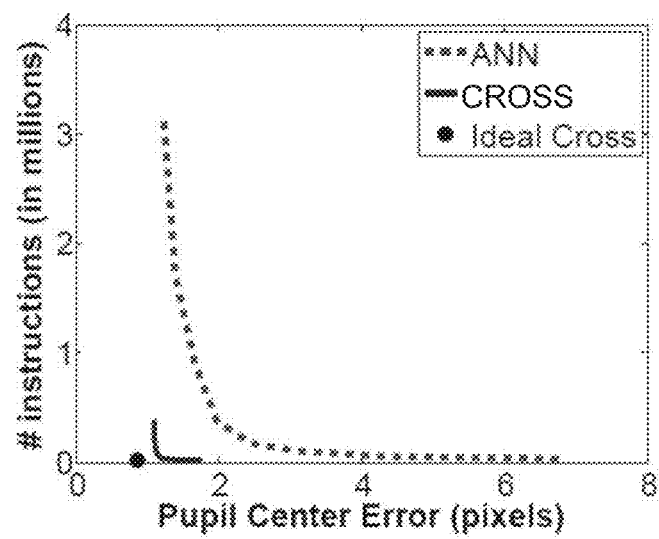
FIG. 9B illustrates a plot of computation cycles versus center accuracy according to the invention.

The performance difference in terms of computation cost is substantial as well, in fact, even more than in the case of sensing (FIG. 9B). The neural network computation is much more involved than the cross model, so there are significantly more operations per pixel. In addition, since the cross model requires fewer pixels, the number of times the computation needs to be performed is also much lower. Thus, the number of instructions that need to be computed for the cross model is orders of magnitude lower than for the neural network.

Figure 9C:
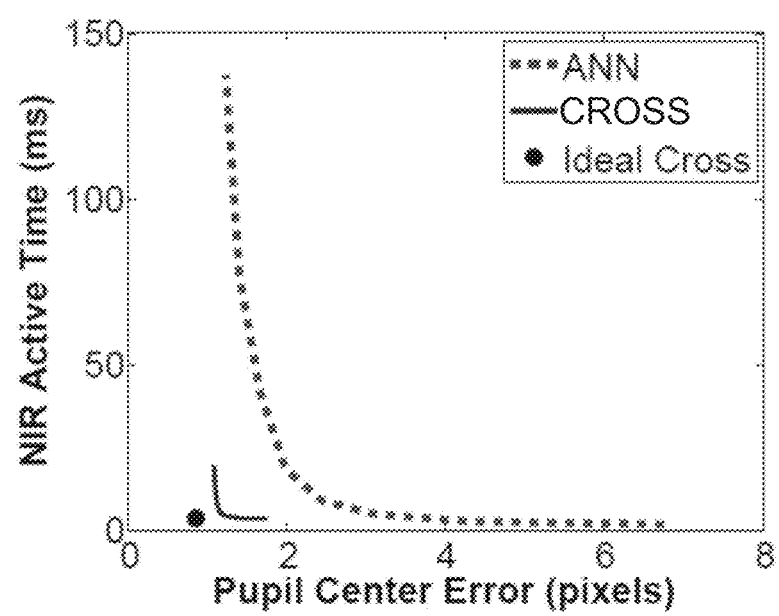
FIG. 9C illustrates a plot of NIR time versus center accuracy according to the invention.

Finally, the time spent with the NIR LED on is also substantially lower for the idealized cross and cross models (FIG. 9C). Since the cross model needs very little time to sense, the NIR LED needs to be turned on for a minuscule amount of time for each frame.

The benefits in sensing, computation and NIR translate into energy savings. The average power was measured over a 10 second window of operation using a DAQ running at a 10 kHz sampling rate. To measure power consumption for all three models, the pixel capture+predict rate of the system was fixed to 4 Hz by inserting MCU sleep periods as needed. The 4 Hz rate is chosen in order to measure a sufficiently large range of neural network model sizes to plot the pareto optimal graph.

Figure 10:
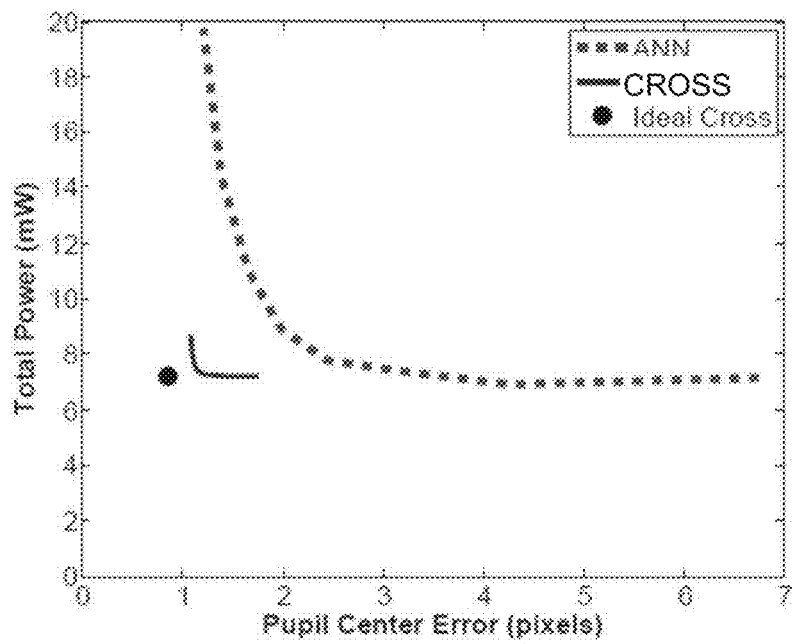
FIG. 10 illustrates a plot of aggregate power versus accuracy according to the invention.

FIG. 10 shows the aggregate power consumption of the invention and compares against the two other baselines. As seen, the invention operates in between the idealized cross and ANN model with roughly a 3× reduction (compared to neural network models that have low error). The overall power budget for the invention is roughly 7 mW, which is a huge improvement over current system and methods, and a substantial achievement considering that the system is operating a camera, estimation algorithm, and NIR LED.

One curious feature of the graph is that the baseline for all schemes is shifted by about 6 mW. The baseline shift corresponds to constant overheads incurred and for configuring various parameters for the camera upon wakeup and shutdown. However, it is contemplated that this constant overhead can be eliminated with a more optimized computational block such as an FPGA rather than a general-purpose MCU.

Figure 11:
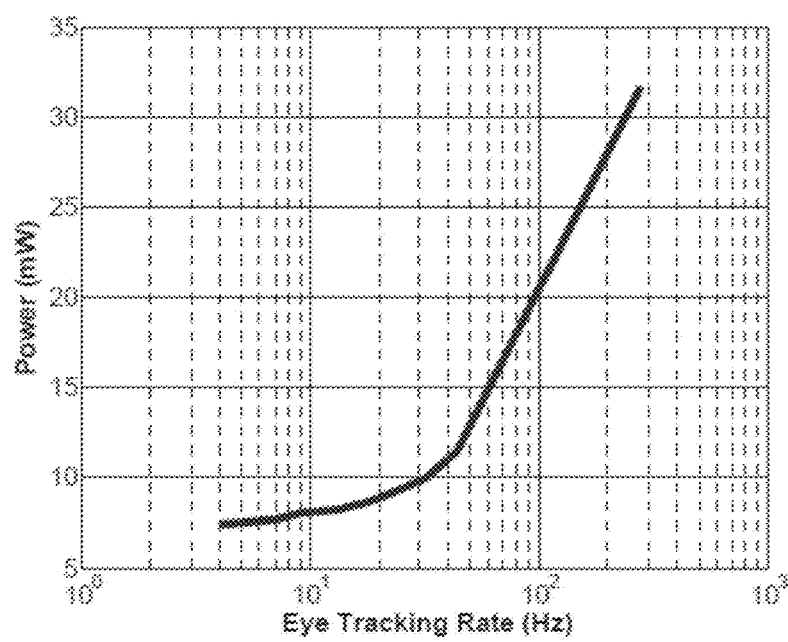
FIG. 11 illustrates a plot of aggregate power versus eye tracking rate (log scale) according to the invention.

Another benefit of the invention is that it can achieve high tracking rates. FIG. 11 illustrates the aggregate power versus eye tracking rate which shows the total system power consumed as the tracking rate is varied.

FIG. 12 shows a finer-grained breakdown of the power versus tracking rate for each component (with a moderately large neural network chosen to use 10% of the pixels). Two power measurements are given—one taken at the maximum eye tracking rate possible for this model size, namely, 278 Hz, and one taken at the 4 Hz rate used for the rest of the evaluation results. There are several useful observations that can be made from this result. Interestingly, the camera and NIR consume virtually no power compared to other components since they are turned on for a very tiny amount of time. The acquisition consumes a significant amount of power because digitization of the analog signal output from the camera is expensive. One of the major improvements that the invention provides is reduction of the digitization overhead. The MCU computation is also expensive, however it is contemplated that some of this cost could be reduced by using a more optimized computation block such as an FPGA.

The invention achieves pupil center estimation accuracy within 1.2 pixels. The neural network method cannot achieve such accurate estimation even when consuming considerably more power and resources. This result may seem surprising at first, since it is natural to expect a more power-hungry technique to have a corresponding increase in performance. The main reason is that the NIR-illuminated eye (indoors) presents very strong edges that are easier to accurately identify using edge detection techniques (the cross model) than using a neural network. So, the accuracies tend to be higher even though the power consumption is much lower. This is not the case in the outdoor environment, however, hence the need for the indoor-outdoor switching model.

FIG. 13 shows the results for pupil size estimation when using only the neural network and when using the invention. The entire power-accuracy profile for pupil size is not shown since it is found that even the smaller ANN models perform well in estimating the pupil size, and there is not much difference in using a larger model. Therefore, only the mean performance across all model sizes is presented. It is seen that the pupil size estimation error is typically less than one pixel, suggesting that both stages can do an excellent job in estimating pupil size.

The invention is now evaluated under conditions with more variability: a) variability in the pupil dilation of the user, b) an outdoor setting with variable illumination, and c) the user moving from an indoor to an outdoor setting.

Figure 14:
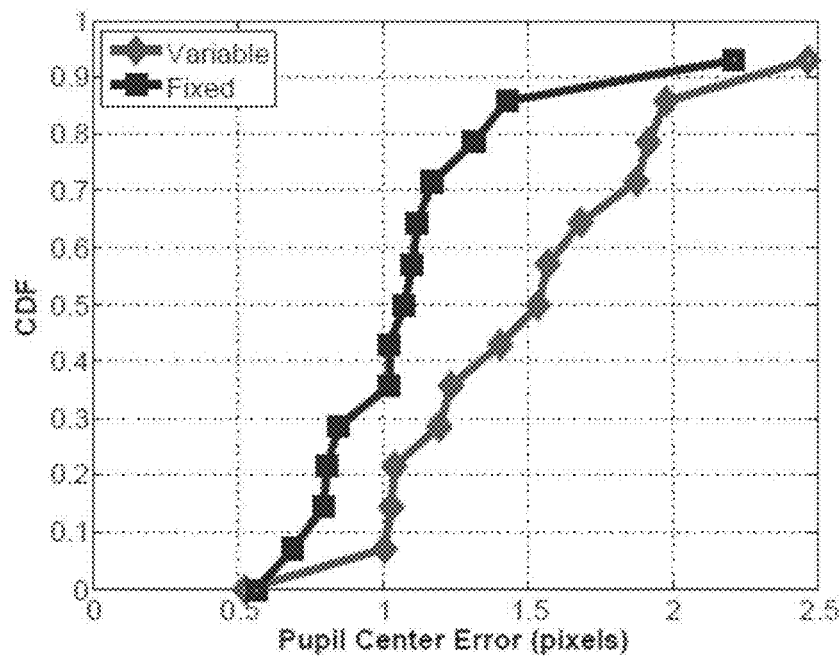
FIG. 14 illustrates a plot of a performance comparison of fixed and variable pupil center according to the invention.
Figure 15:
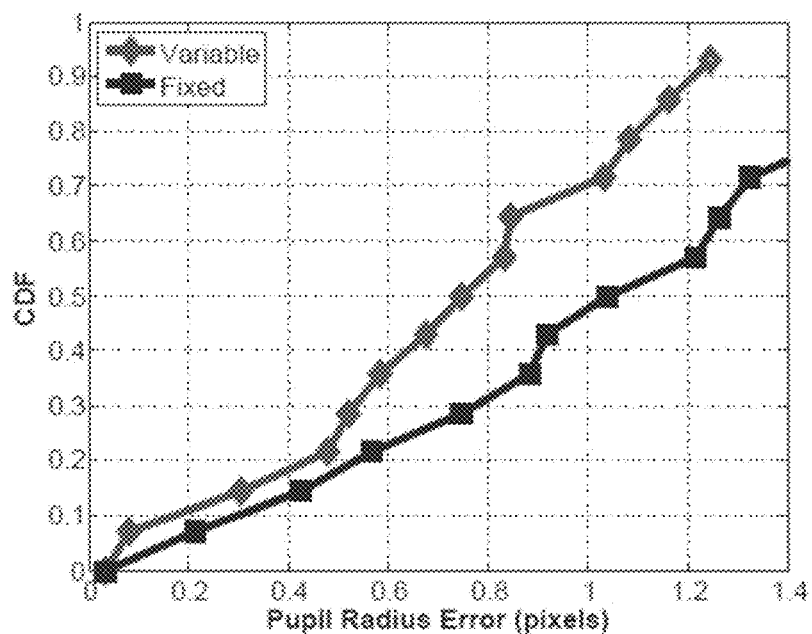
FIG. 15 illustrates a plot of a performance comparison of fixed and variable pupil size according to the invention.

With respect to variable pupil dilation, the pupil center and pupil size estimation errors for the 14 users in the indoor-variable dataset are compared, all of whom are also in the indoor-stable dataset. FIG. 14 compares the pupil center prediction results for fixed and variable illumination conditions, each as an error CDF, and FIG. 15 gives the same comparison for size prediction. The center prediction accuracy under varying pixel sizes is marginally worse than the accuracy under fixed pixel sizes, but the difference is not significant. For the size prediction task, the invention actually generated slightly better estimates on the variable pupil size dataset. This seems counter-intuitive at first, however, in the indoor-variable dataset, the pupil size is generally larger than in indoor-stable, as the lighting conditions were darker.

This makes accurate detection of the size slightly easier for both the ANN and the cross model.

The outdoor scenario represents another high variability situation for the invention. The cross model does not work in this situation, so the system relies primarily on the neural network that is trained for outdoor settings. The accuracy under outdoor settings is roughly 4 pixels (for moderately sized ANNs). The results are worse than accuracy in indoor settings, but not far off. In fact, the accuracy obtained in outdoor settings is better than the results that were obtained in under indoor settings. One of the main reasons for the performance difference is the vastly improved labeling pipeline allowing the labeling of noisy data quite well.

About 1 pixel pupil dilation error is realized but this is an over-estimate of the real error for reasons described above. There is about a 1 pixel offset between the radius estimated by the offline labeling algorithm (which performs filtering), and by the cross model.

Figures 16, 17:
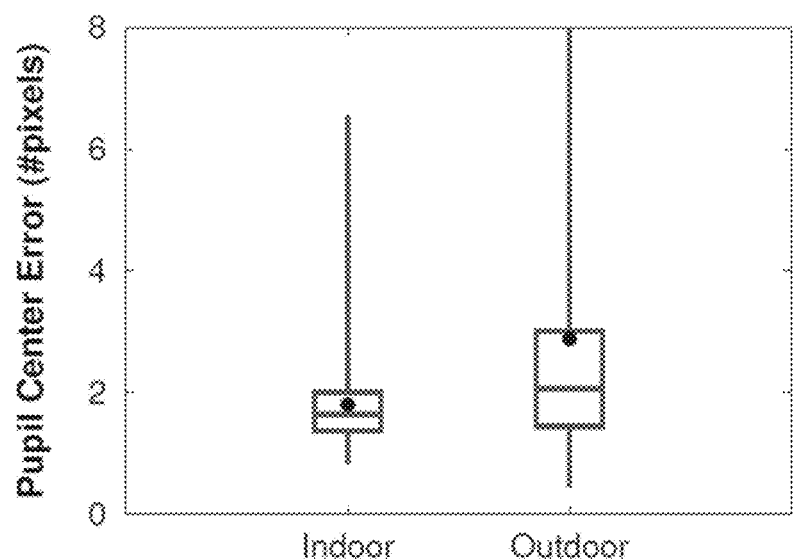
FIG. 16 illustrates a plot of indoor-outdoor switching according to the invention.
FIG. 17 illustrates a table of automatic labeling versus hand labeling of the pupil according to the invention.

Now turning to the situation where a user is moving between an indoor and outdoor environment, FIG. 16 shows the error distribution during the indoor segments versus outdoor segments. This is shown as a box plot, where the three lines in the box corresponds to the quartiles (25 percentile, median, and 75 percentile), the whiskers correspond to the max and min, and the dot is the mean. It is also verified from the traces that the NIR-based switching works effectively, and switches models between the indoor and outdoor modes whenever the user changes environments. As observed in previously, the instruction cycle and power cost of the detection and switching process itself is negligible. The error distribution of the predictions is higher for the outdoor case, but it is still relatively low with a mean of less than three pixels. The error when indoors is lower with a mean of less than two pixels.

One of the major benefits of the invention is the eye tracking speeds that it can achieve. High-speed eye tracking is useful for understanding fast saccadic movements of the eye, which is one of the neural mechanisms for maintaining visibility. For example, one of the interesting use-cases for measuring micro saccades is as a diagnostic test for ADHD, and there are other applications of such measurements. To evaluate the maximum speed achievable by the invention, it was run continuously on a tracking device without duty-cycling. The rate at which pupil center measurements were generated achieved frame rates of 250-350 Hz (depending on whether a medium-sized or small ANN is used). These speeds are comparable to the rates achieved by high-speed eye trackers. One caveat is that the invention is not uniformly sampling since it occasionally uses the ANN. However, the irregularity during the use of ANN can be mitigated by using a smaller ANN model. The power consumption at this frame rate is several tens of milliwatts since the system is operating in always ON mode. Therefore, many of the optimizations may no longer work. However, the high-speed mode is not anticipated to be used continuously; rather, this mode may be triggered when appropriate.

To evaluate the accuracy of the labeling scheme 100 eye images were hand-labeled from one subject's data. For each image, an elliptical region was selected that visually seemed size estimate with those provided by the automatic labeling system for the same frames. The results are given in FIG. 17. Note that for both measures, the hand-labeling and automatic labeling techniques yield very similar results. The pupil size is slightly higher, but this is most likely due to the fact that the low-resolution images do no provide as sharp of an edge as would be expected with a higher-resolution camera. Thus, the pupil edge appears spread over a one- to two-pixel area, and distinguishing the exact pupil boundary within that region is difficult for a human to do visually.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A system for tracking parameters of an eye, the system comprising:
   an imaging component facing at least said eye and positioned to image a pupil of said eye;
   a controller operably connected to the imaging component, the controller performing the steps of:
      obtaining a subsampling of a set of pixels of a pupil image gathered from said imaging component;
      estimating, based on said subsampled set of pixels, a location parameter based on a center of said pupil according to a x coordinate and a y coordinate and a size parameter according to a radius r of said pupil, wherein said estimating step further comprises the step of using an artificial neural network prediction model; and
      tracking said pupil by sampling a row and a column of pixels based on said estimated location parameter and said estimated size parameter of said pupil, wherein said tracking step further comprises the steps of validating the sampled pixels with the pupil image, and using validated sampled pixels to track parameters of the eye.

2. The system of claim 1 wherein said tracking step performed by the controller further comprises the steps of: median filtering said row and said column of pixels, detecting regions of said eye using edge detection, finding a midpoint of said row and said column of pixels, performing a validity check to determine said midpoint is consistent, and if the validity check shows an error, said controller repeats said estimating step and said tracking step.

3. The system of claim 1 further comprising a computing device, wherein the controller further comprises the steps of: calibrating the artificial neural network by capturing images of said eye in at least one lighting condition; communicating by the controller said images to the computing device, wherein said computing device performs said estimating step and said tracking step to form a signature of said eye in said at least one lighting condition.

4. The system of claim 1 further comprising an infrared photodiode that detects at least one lighting condition.

5. The system of claim 1 further comprising an infrared illuminator positioned to illuminate said eye.

6. The system of claim 3 wherein said calibrating step is completed automatically.

7. The system of claim 1 wherein said controller omits said tracking step when at least one lighting condition is outdoors and said controller performs the step of increasing a quantity of said subsampled set of pixels of said obtaining step.

8. A method for tracking parameters of an eye comprising the steps of:
   providing a camera facing at least said eye and positioned to capture an image of a pupil of said eye;
   obtaining by a controller a subsampling of a set of pixels gathered from the image;

estimating by the controller, based on said subsampled set of pixels, a location parameter based on a center of said pupil according to a x coordinate and a y coordinate and a size parameter according to a radius r of said pupil, wherein said estimating step further comprises the step of using an artificial neural network prediction model; tracking by the controller said pupil by sampling a row and a column of pixels from the image based on said estimated location parameter and said estimated size parameter, wherein said tracking step further comprises the steps of validating the sampled pixels with the image, and using validated sampled pixels to track parameters of the eye.

9. The method of claim 8 wherein said tracking step further comprises median filtering said row and said column of pixels, detecting regions of said eye using edge detection, finding the midpoint of said row and said column of pixels, performing a validity check to determine said midpoint is consistent, and if the validity check shows an error, said system repeats said estimating step and said tracking step.

10. The method of claim 8 further comprising the step of calibrating by the controller the artificial neural network prediction model by capturing images of said eye in at least one lighting condition; communicating said images to a computing device, wherein said computing device performs said estimating step and said tracking step to form a signature of said eye in said at least one lighting condition.

11. The method of claim 10 further comprising the step of hard-coding by the controller said signature into said controller for use in said estimating step.

12. The method of claim 11 further comprising the step of detecting by an infrared photodiode said at least one lighting condition.

13. The method of claim 8 further comprising the step of illuminating by an infrared illuminator said eye.

14. The method of claim 10 wherein said calibrating step is completed automatically.

15. The method of claim 8 wherein said tracking step is omitted when said at least one lighting condition is outdoors and further comprising the step of increasing a quantity of said subsampled set of pixels of said obtaining step.

16. The system of claim 1 wherein the artificial neural network prediction model is:

$$\hat{X} = B_x^O + \sum_{k=1}^{K} W_{kx}^{WO} H_k$$

$$\hat{Y} = B_y^O + \sum_{k=1}^{K} W_{ky}^{HO} H_k$$

$$\hat{R} = B_r^O + \sum_{k=1}^{K} W_{kr}^{HO} H_k$$

$$H_k = \tanh\left(B_k^H + \sum_{i=1}^{D} \sum_{j=1}^{D} W_{ijk}^{IH} I_{ij}\right)$$

$I_{ij}$ represents a pixel at row i and column j of the pupil image, $H_k$ represents K hidden units, $W_{ijk}^{IH}$ represents input-to-hidden parameters for each pixel location (i,j) and each hidden unit $H_k$, $B_K^H$ represents a hidden unit bias parameter for each hidden unit $H_k$, $W_{kx}^{HO}$ and $W_{ky}^{HO}$ represent hidden-to-output parameters mapped between hidden unit $H_k$ and the x coordinate and the y coordinate and the radius r, and $B_x^O$, $B_y^O$, $B_r^O$ represent output bias parameters for the x coordinate and the y coordinate and the radius r.

17. The method of claim 8 wherein the artificial neural network prediction model of said using step is:

$$\hat{X} = B_x^O + \sum_{k=1}^{K} W_{kx}^{WO} H_k$$

$$\hat{Y} = B_y^O + \sum_{k=1}^{K} W_{ky}^{HO} H_k$$

$$\hat{R} = B_r^O + \sum_{k=1}^{K} W_{kr}^{HO} H_k$$

$$H_k = \tanh\left(B_k^H + \sum_{i=1}^{D} \sum_{j=1}^{D} W_{ijk}^{IH} I_{ij}\right)$$

$I_{ij}$ represents a pixel at row i and column j of the pupil image, $H_k$ represents K hidden units, $W_{ijk}^{IH}$ represents input-to-hidden parameters for each pixel location (i,j) and each hidden unit $H_k$, $B_K^H$ represents a hidden unit bias parameter for each hidden unit $H_k$, $W_{kx}^{HO}$ and $W_{ky}^{HO}$ represent hidden-to-output parameters mapped between hidden unit $H_k$ and the x coordinate and the y coordinate and the radius r, and $B_x^O$, $B_y^O$, $B_r^O$ represent output bias parameters for the x coordinate and the y coordinate and the radius r.

* * * * *